United States Patent [19]

Marshall et al.

[11] Patent Number: 5,086,165

[45] Date of Patent: Feb. 4, 1992

[54] INHIBITORS OF RETROVIRAL PROTEASE WITH A KETOMETHYLENE ISOSTERIC REPLACED AMIDE BOND

[75] Inventors: Garland R. Marshall, Clayton; Mihaly V. Toth, Kirkwood, both of Mo.

[73] Assignee: Washington University, St. Louis, Mo.

[21] Appl. No.: 652,163

[22] Filed: Feb. 7, 1991

Related U.S. Application Data

[63] Continuation-in-part of Ser. No. 320,742, Mar. 8, 1989.

[51] Int. Cl.$^5$ .................... A61K 37/02; C07K 7/06
[52] U.S. Cl. ................................ 530/329; 530/330
[58] Field of Search ..................... 530/328; 330/329

[56] References Cited

FOREIGN PATENT DOCUMENTS 301570 2/1989 European Pat. Off. .

OTHER PUBLICATIONS

Schneider et al., Cell (54), 1988, pp. 363–368.
Holladay et al, J. Med. Chem. (30), 1987, pp. 374–383.
Billich et al, J. Biol. Chem. (263), No. 34, 1988, pp. 17905–17908.
Harbeson et al, J. Med. Chem. 1989, (32) 1378–1392.
Korant et al., J. Cell. Biochem. 32, 91–95 (1986).
Rich, in Barrett and Salvesen, eds., Elsevier Sci. Publ. 1987, pp. 179–287.
Katoh et al., Nature 329, 654–656 (1987).
Krausslick et al., J. Virology 62, 4393–4397 (1988).
Nutt et al., Proc. Natl. Acad. Sci. U.S.A. 85, 7179–7233 (1988).
Seelmeier et al., Proc. Natl. Acad. Sci. U.S.A. 85, 6612–6616 (1985).
Kohl et al., Proc. Natl. Acad. Sci. U.S.A. 85, 4686–4690 (1988).
Darke et al., Biochem. Biophys. Res. Commun. 156, 297–303 (1988).
Kotler et al., Proc. Natl. Acad. Sci. U.S.A. 85, 4185–4189 (1988).
J. Kaltenbronn et al., J. Med. Chem. 33, 838–845 (1990).
Pearl and Taylor, Nature 326, 482 (1987).
Toh et al., Nature 315, 691 (1985).

*Primary Examiner*—Lester L. Lee
*Assistant Examiner*—S. G. Marshall
*Attorney, Agent, or Firm*—Scott J. Meyer; James W. Williams, Jr.

[57] ABSTRACT

Disclosed herein are compounds of the class of peptides having from about 4 to about 8 amino acid residues that are substrates for retroviral protease, e.g., HIV protease, derived from known cleavage sites and that are modified to contain an internal $COCH_2$ bond isostere, useful as inhibitors of said retroviral protease, e.g., HIV protease, and exemplified by the modified peptide, Abz-Thr-Ile-NleΨ(K)Nle-Gln-Arg-$NH_2$, wherein K is $COCH_2$.

1 Claim, No Drawings

INHIBITORS OF RETROVIRAL PROTEASE WITH A KETOMETHYLENE ISOSTERIC REPLACED AMIDE BOND

CROSS-REFERENCE TO RELATED APPLICATION

This is a continuation-in-part of copending application Ser. No. 07/320,742, filed Mar. 8, 1989.

BACKGROUND OF THE INVENTION

This invention relates to novel inhibitors of retroviral protease. More particularly, the invention is concerned with ketomethylene isosteric replaced amide bond modified peptide inhibitors of retroviral protease such as human immunodeficiency virus (HIV) protease. As such, these inhibitors have potential use for the treatment of acquired immune deficiency syndrome (AIDS) and aids related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., *Science* 224, 500–503 (1984), and Popovic et al., *Ibid.*, 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his co-workers in 1986 [*Nature* 326, 662 (1987)]. As used herein HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name, azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

Another approach being investigated recently for potential use in the treatment of AIDS is the development of synthetic peptides as inhibitors of retroviral protease. Thus, it is known that retroviruses, including the human immunodeficiency virus (HIV), express their genetic content by directing the synthesis of a polyprotein by the host. This precursor is then processed by proteolysis to give essential viral enzymes and structural proteins. A virally encoded enzyme, the retroviral protease, is contained within the polyprotein and is responsible for the specific cleavages of the polyprotein yielding mature viral proteins. See, for example, Krausslich and Wimmer, *Ann. Rev. Biochem.* 57, 701–754 (1988).

Inhibition of the HIV protease as a means of therapeutic intervention in the treatment of AIDS and ARC patients is a logical strategy. Inhibition of virally encoded proteases as an approach to antiviral therapy has been demonstrated by Korant et al., *J. Cell. Biochem.* 32, 91–95 (1986), who showed that an endogenous inhibitor of cysteine proteases, cystatin, inhibited replication of poliovirus in tissue culture. A number of observations in the last few years serve to rationalize this approach for HIV. Isolation and sequence analysis of the HIV-1 [Ratner et al., *Nature* 313, 277–284 (1985)] and HIV-2 [Guyader et al., *Nature* 326, 662–669 (1987)] viral genomes show homology of a segment [Toh et al., *Science* 231, 1567 (1986)] with other retroviral proteases [Yasumaga et al., *FEBS Lett.* 199, 145 1986)] which show limited homology with a known class of proteolytic enzyme, the aspartic proteinases [Rich, "Inhibitors of aspartic proteinases" in *Proteinase Inhibitors*, Barrett and Salvesen, eds., Elsevier Science Publ., Amsterdam, 1987, pp. 179–217]. This includes the presence of a conserved Asp-Thr-Gly sequence characteristic of the active site of aspartic proteinases. Known inhibitors of this class of enzyme (pepstatin at high concentration and DAN) inhibit the protease activity of avian myeloblastosis virus [Dittmar and Moelling, *J. Virology* 28, 106 (1978)], bovine leukemia, Maloney murine leukemia and human T-cell leukemia viruses as shown by Dittmar and Moelling, supra. and by Katoh et al., supra. Several groups [Hansen et al., *J. Virology* 62, 1785–1791 (1988) and Krausslich et al., *Ibid.* 62, 4393–4397 (1988)] have demonstrated inhibition by pepstatin of processing of gag-pol polyprotein by HIV protease. Nutt et al., *Proc. Natl. Acad. Sci. USA* 85, 7179–7233 (1988), reported that pepstatin inhibited synthetic HIV protease with a $K_i = 1.4$ μmolar. This link to aspartic proteinases presents the opportunity to draw upon the knowledge-base gathered on renin, the most prominent aspartic proteinase, to expedite the development of specific and potent inhibitors of HIV proteases.

The HIV protease has been shown to be essential in the maturation of viral proteins necessary for viral multiplication such as the gag core proteins when expressed in yeast [Kramer et al., *Science* 231, 1580 (1986)] or the reverse transcriptase (RT) when expressed in *E. coli* [Farmerie et al., *Science* 263, 305 (1987)]. Modification by Seelmeier et al., *Proc. Natl. Acad. Sci. USA* 85, 6612–6616 (1988), and by Mous, et al., *J. Virology* 62, 1433–1436 (1988), of the aspartic residue (Asp-25) corresponding by sequence homology to the active site residue by site-directed mutagenesis prevents processing of the polyprotein. Kohl et al., *Proc. Natl. Acad. Sci. USA* 85, 4686–4690 (1988), have also shown in an *E. coli* expression system that the replacement of Asp-25 with Asn in HIV protease prevents cleavage of gag p55 in cultured cells and inhibits infectivity in tissue culture. Loeb et al., *J. Virology* 63, 111–121, (1989) have carried out an extensive mutagenesis study on HIV protease expressed in *E. coli* and shown inhibition of gag processing by both conservative and non-conservative mutation of the amino acids adjacent to the assumed active site. This demonstrates in HIV a similar role for the protease to that shown by Katoh et al., *Virology* 145, 280-292 (1985), for Maloney murine leukemia virus where deletions in the protease region led to immature virus particles with markedly reduced infectivity.

Modification of known substrate sequences is an accepted approach to inhibitor generation. HIV protease cleaves the virally encoded polyprotein at several sites to liberate the gag proteins (p17,p24,p15) as well as the protease (Prot) itself and reverse transcriptase (p66). Thus, small peptides overlapping each of the cleavage sites (p17/p24, p24/p15, p15/Prot, and Prot/p66) become candidates for modification. Schneider and Kent, *Cell* 54 363 (1988), have prepared peptide substrates of twenty or more residues corresponding to each of these cleavage sites and demonstrated that their synthetic enzyme cleaved at the appropriate site. Darke et al., *Biochem. Biophys. Res. Commun.* 156, 297-303 (1988), showed that both expressed and synthetic enzyme cleaved at the proposed processing sites with larger synthetic peptides. Cleavage of VSQNYPIV, corresponding to the cleavage site between gag p17 and gag p24, occurred at the same rate as a fifteen residue substrate with a $K_m=2.5$ mM. The minimal length peptide substrate that was shown to be cleaved (at 90% of the rate of the octapeptide) was a heptapeptide, SQNY-PIV. Either SQNY-PI, QNY-PIV, or acetyl-QNY-PIV failed to be cleaved. In studies on the protease from the retrovirus, avian sarcoma-leukosis virus (ASLV), Kotler et al, *Proc. Natl. Acad. Sci. USA* 85, 4185-4189 (1988), examined decapeptide substrates and suggest that the minimal size for cleavage with ASLV protease is longer than six residues. An unspecified hexapeptide corresponding to a sequence of HIV containing a Tyr-Pro cleavage site was reported to be a relatively poor substrate and act as an inhibitor of the cleavage of better substrates of ASLV protease.

DESCRIPTION OF THE INVENTION

In accordance with the present invention, novel inhibitors of retroviral protease are provided. These inhibitors are ketomethylene isosteric replaced amide bond modified peptides of relatively short amino acid chain length of from about 4 to about 8 amino acid residues, and preferably are hexapeptides and heptapeptides. These inhibitors contain an internal ketomethylene isostere, $\Psi[COCH_2]$, as an amide replacement in the peptide. The preferred peptide inhibitors are based on substrates for HIV protease derived from HIV-1 and HIV-2 known cleavage sites and modified to contain the $\Psi[COCH_2]$ isostere. The following illustrate the preferred peptide inhibitors of HIV protease.

Peptide

Abz-Thr-Ile-Nle$\Psi$(K)Nle-Gln-Arg-NH$_2$
Abz-Thr-Ile-Nle-$\Psi$(K)2-Nal-Gln-Arg-NH$_2$
Abz-Thr-Ile-Phe$\Psi$(K)Ala-Gln-Arg-NH$_2$
Qua-Thr-Ile-Nle$\Psi$(K)2-Nal-Gln-Arg-NH$_2$
Qua-Ile-Nle$\Psi$(K)2-Nal-Gln-Arg-NH$_2$
Qua-Nle$\Psi$(K)2-Nal-Gln-Arg-NH$_2$
Qui-Thr-Ile-Nle$\Psi$(K)Nle-Gln-Arg-NH$_2$
Qui-Ile-Nle$\Psi$(K)Nle-Gln-Arg-NH$_2$
Qui-Nle$\Psi$(K)Nle-Gln-Arg-NH$_2$
Qui-Thr-Ile-Nle$\Psi$(K)2-Nal-Gln-Arg-NH$_2$
Qui-Ile-Nle$\Psi$(K)2-Nal-Gln-Arg-NH$_2$
Qui-Nle$\Psi$(K)2-Nal-Gln-Arg-NH$_2$
Qui-Thr-Ile-Nle$\Psi$(K)2-Nal-Gln-NH$_2$
Qui-Ile-Nle$\Psi$(K)2-Nal-Gln-NH$_2$
Qui-Nle$\Psi$(K)2-Nal-Gln-NH$_2$
K=COCH$_2$

The novel inhibitors of HIV protease and other such retroviral proteases can be prepared by known solution and solid phase peptide synthesis methods. For introducing the COCH$_2$ bond isostere, the general synthesis method of Kaltenbronn et al., *J. Med. Chem.* 33, 838-845 (1990), is suitable for preparing a keto-methylene dipeptide. This five step synthesis includes the conversion of the Boc-protected amino acid to its corresponding bromo-ketone through a diazoketo intermediate. The bromide is displaced by the anion of malonic ester which affords a doubly activated hydrogen at which the side chain of the $P_1'$ position is introduced. The malonic ester derivative is treated with NaH followed by subsequent addition of alkyl iodides and bromides. Then hydrolysis and decarboxylation of the malonic ester delivers a diastereomeric mixture of the dipeptide unit. This keto-methylene dipeptide is then incorporated as a unit in a conventional solution or solid phase procedure for peptide synthesis.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxypthalimide or N-hydroxy-succinimide, and the various cleavage reagents, e.g., trifluoroacetic acid, HCL in dioxane, boron tris-(trifluoracetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or p-methylbenzhydrylamine polymer. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco; 1969, and the review chapter by Merrifield in *Advances in Enzymology* 32, pp. 221-296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

In order to illustrate specific preferred embodiments of the invention in greater detail, the following exemplary laboratory preparative work was carried out.

EXAMPLE 1

Synthesis of peptide
Qui-Thr-Ile-NleΨCOCH$_2$]2-Naphtylala-Gln-Arg-NH$_2$

1) Solid Phase Synthesis of the Peptide

The peptide was prepared by solid phase synthesis using the p-methylbenzhydrylamine polymer (0.33 g, 0.33 mmol). The following synthetic protocol was used for the incorporation of the Boc-amino acids:

Deprotection:
  TFA (10 mL), 1 minute.
  TFA (10 mL), 5 minutes.
  DMF (10 mL), 2×2 minutes.

Neutralization:
  DIPEA (10 mL,10% in DMF), 2 minutes.
  DMF (10 mL), 2×2 minutes.

Coupling:
  4 equivalents of Boc-amino acid, 4 equivalents of benzotriazol-1-yloxy-tris-(dimethylamino)-phosphonium hexafluorophosphate (BOP reagent) and 12 equivalents of DIPEA in DMF (10 mL) for 1 hour.
  The coupling in DMF is repeated if the Kaiser test is positive.
  The dipeptide analog containing the keto-methylene isostere was incorporated in this protocol as a unit and its synthesis is described below.

Cleavage:
  HF/anisole (9:1) procedure of Tam et al, *J. Am. Chem. Soc.* 105, 6442–6455 (1983).
  Dissolvation of crude peptide in 30% acetic acid and lyophilization.

Purification:
  Reverse-phase HPLC on a C-18 semipreparative column using water at CH$_3$CN as solvents.

2) Solution Phase Synthesis of the Dipeptide Analog Containing the Keto-Methylene Isostere The synthesis of the dipeptide analog containing the keto-methylene isostere is described in Scheme 1, below. The procedure of Kaltenbronn et al., *J. Med. Chem.* 33, 838–845 (1990), was used.

(S)-(1-Butyl-3-diazo-2-oxopropyl)carbamic acid, 1.1-Dimethylethyl Ester 1

A solution of Boc-Norleucine (6.9 g, 30 mmol) in ethyl acetate (EtOAc) (80 mL) was cooled to −25° C. and N-methylmorpholine (3.3 mL, 30 mmol) was added followed by isobutyl chloroformate (4.2 mL, 32 mmol). The mixture was stirred for 15 minutes at −25° C. and diethylether (Et$_2$O) (50 mL) was then added. After cooling the mixture to −50° C., the white precipitate was filtered under N$_2$ and the cold filtrate was treated with a solution of diazomethane in Et$_2$O (130 mL, 0.4 M, 52 mmol). The mixture was allowed to proceed overnight, gradually warming up to room temperature. Excess of diazomethane was removed by bubbling a N$_2$ stream through the solution and the solvent was then evaporated. The residual oil was dissolved in EtOAc (100 mL) and was washed with saturated NaHCO$_3$ (1×100 mL) and brine (1×100 mL). The organic layer was dried over Na$_2$SO$_4$, filtered and concentrated to yield 7.5 g (98)% of crude product.

(S)-(3-Bromo-1-butyl-2-oxopropyl)carbamic Acid, 1.1-Dimethylethyl Ester 2

A solution of diazoketone 1 (7.5 g crude, 29.4 mmol) in EtOAc (100 mL) was cooled to −20° C. and HBr gas was bubbled in until no more N$_2$ gas evolved (about 20 minutes). The mixture was poured on saturated NaHCO$_3$ and extracted with EtOAc. The combined organic layers were washed with saturated NaHCO$_3$ (2×100 mL) and brine (1×100 mL), dried over Na$_2$SO$_4$, filtered and concentrated. The residue was recrystallized from hexane to afford 7.5 g (83%) of product.

2-[3[(1,1-Dimethylethoxy)carbonyl]-aminol-2-oxoheptyl]propanedioc Acid, Bis(phenylmethyl) Ester 3

A suspension of NaH (1.1 g, 28 mmol, 60% in mineral oil) in hexane was washed free of mineral oil and then suspended in tetrahydrofuran (THF) (40 mL). A solution of dibenzylmalonate (6.1 mL, 24.3 mmol) in THF (50 mL) was added slowly and the solution was stirred for 1 hour and then cooled to 0° C. A solution of bromide 2 (7.5 g, 24.3 mmol) in THF (20 mL) was added and the mixture was stirred at 0° C. for 30 minutes and then at room temperature for 1 hour. The residue was concentrated and then dissolved in EtOAc (100 mL), washed with 1M citric acid (2×100 mL), saturated NaHCO$_3$ (2×100 mL) and brine (1×100 mL). The organic layer was dried over Na$_2$SO$_4$, filtered and concentrated to give 13 g (99%) of crude product.

2-[3-[[(1,1-Dimethylethoxy)carbonyl]-amino]-2-oxoheptyl]2-(2methylnaphtyl)propanedioic Acid, Bis(phenylmethyl) Ester 4

A suspension of NaH (0.55 g, 14.0 mmol, 60% in mineral oil) in hexane was washed free of mineral oil and then suspended in dimethylformamide (DMF) (25 mL). To this suspension was added slowly a solution of malonate 3 (5.1 g, 10 mmol) in DMF (25 mL) and the mixture was stirred for 1 hour at room temperature. The mixture was then treated with a solution of 2-bromomethylnaphtalene (3.3 g, 15 mmol) in DMF (25 mL) and stirred for 12 hours. The solvent was evaporated and the residue was dissolved in EtOAc (100 mL) and washed with 10% KHSO$_4$ (2×100 mL), saturated NaHCO$_3$ (2×100 mL) and brine (1×100 mL). The organic layer was dried over Na$_2$SO$_4$, filtered and concentrated to yield 8.6 g of crude product.

Boc-NleΨ[COCH$_2$]2-Naphtylala 5

A solution of malonate 4 (8.6 g crude) in MeOH (100 mL) was treated with 10% Pd/C and was stirred in a hydrogen atmosphere (40 psi) for 12 hours. The mixture was filtered and the solvent was removed under reduced pressure. The residue was taken up in toluene (100 mL) and heated at reflux for 3 hours. The solvent was removed under pressure and the residue was dissolved in EtOAc (100 mL), washed with 10% KHSO$_4$ (2×100 mL) and brine (1×100 mL). The organic layer was dried over Na$_2$SO$_4$, filtered and concentrated. The residue was recrystallized from EtOAc and hexane (1:3) to afford 1.8 g (42% for 2 steps) of dipeptide.

SCHEME 1

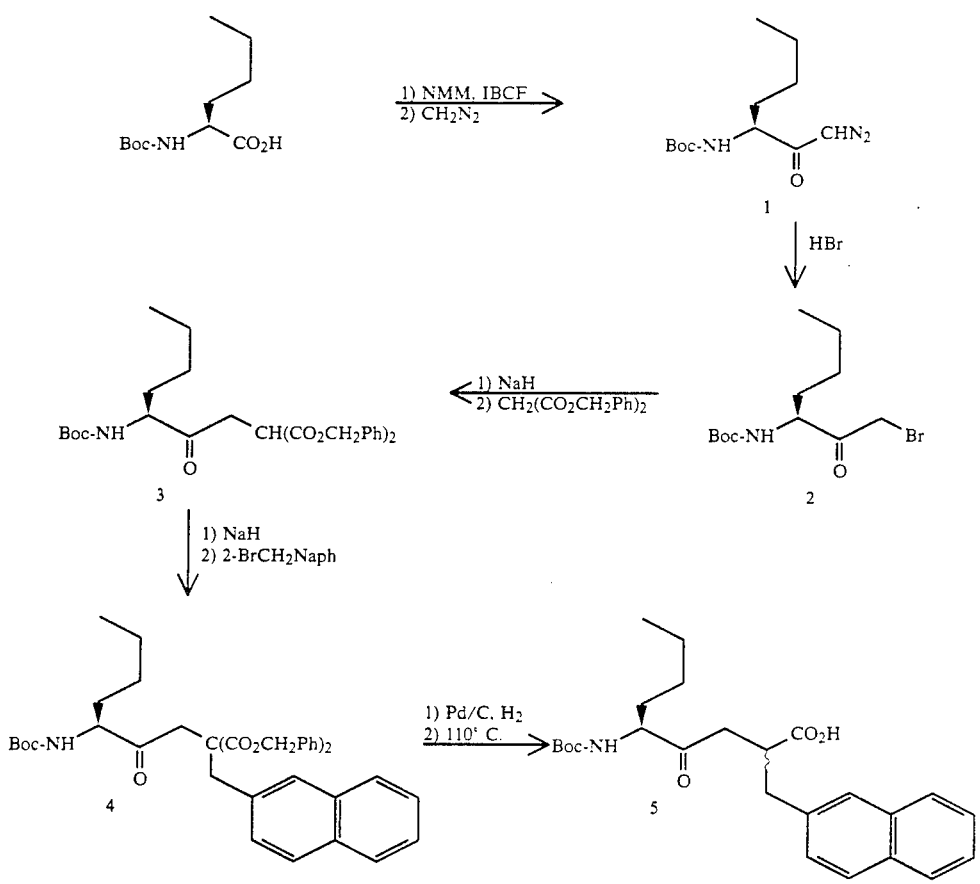

EXAMPLE 2

HIV protease assay. The HIV protease assay was conducted using either synthetic HIV protease [Schneider and Kent, *Cell* 54, 363 (1988)] kindly supplied by Dr. Stephen Kent of Caltech, or cloned material expressed in *E. coli* supplied by Dr. George Glover of the Monsanto Company. In all cases examined, the cleavage patterns and inhibition results were identical. Synthetic protease (1 mg/ml) was dissolved in a buffer (20 mM PIPES, 0.5% NP-40 detergent, 1 mM dithiothreitol), pH 6.5. Substrates were also dissolved in the same buffer at 1 mg/ml concentration. 5 μl of substrate and 5 μl of HIV protease were added to an Eppendorf tube which was centrifuged for one minute and incubated at 25° for the desired time. The reaction was stopped by the addition of 50 μl of 50% TFA. The sample was diluted with 200 μl of water and applied to a C₄ HPLC column developed with 0.1% TFA for 5 min followed by a gradient of 0-50% acetonitrile in 50 min. For inhibitor studies, 5 μl of the protease solution was preincubated for 10 min with the 5 μl of inhibitor (dissolved in 10% DMSO and diluted to 1 mg/ml with buffer). Then 5 μl of test substrate, acetyl-Thr-Ile-Met-Met-Gln-Arg-NH₂ was added in order to determine inhibition of cleavage. Reactions were stopped as above and cleavage rates were monitored by HPLC as above.

Substrate analogs were prepared in order to examine the relative hydrolysis rates of the various sites. As an objective was the development of potential therapeutic agents, a minimal size for recognition was desired as illustrated by hepta- and hexapeptide substrates (Table 1). In contrast to the reports of Darke et al., supra, and Kotler et al., supra, hexapeptides were found to function as good substrates provided that their charged amino and carboxyl termini are blocked such as, for example, with acetyl and amide groups, respectively, although this is not essential to activity. The p24/p15 hexapeptide Ac-Thr-Ile-Met-Met-Gln-Arg-NH₂, was characterized with a $K_m$ 32 1.4 mM and a $V_{max}$ 32 725 nmoles/min/mg. This compares favorably with the data of Darke et al., supra, for most of the longer peptide substrates. Relative cleavage rates were measured by comparing the percent of a standard substrate concentration cleaved by the same concentration of enzyme in twenty minutes (linear portion of curve).

TABLE 1.

| Cleavage Site | Substrates for HIV protease derived from HIV-1 or HIV-2 known cleavage sites. | |
|---|---|---|
| | Peptide | Relative Rate |
| p17/24 (HIV2) | Ac—Gln—Asn—Tyr—Pro—Ile—Val—NH₂ | 0.04 |
| | Ac—Gly—Asn—Tyr—Pro—Val—Gln—NH₂ | |
| p24/p15 | Ac—Thr—Ile—Met—Met—Gln—Arg—NH₂ | 1.00* |
| | Ac—Thr—Ile—Nle—Hle—Gln—Arg—NH₂ | 0.95 |

TABLE 1.-continued

Substrates for HIV protease derived from HIV-1 or HIV-2 known cleavage sites.

| Cleavage Site | Peptide | Relative Rate |
|---|---|---|
| | Ac—Thr—Ile—PnF—Nle—Gln—Arg—NH$_2$ | — |
| | Ac—Thr—Ile—Nle—PnF—Gln—Arg—NH$_2$ | 0.57 |
| | Aba—Thr—Ile—Nle—PnF—Gln—Arg—NH$_2$ | 1.46 |
| p15/Prot | Ac—Phe—Asn—Phe—Pro—Gln—Ile—NH$_2$ | — |
| | Ac—Ser—Phe—Asn—Phe—Pro—Gln—Ile—NH$_2$ | — |
| (HIV2) | Ac—Leu—Ala—Ala—Pro—Gln—Phe—NH$_2$ | — |
| Prot/p66 | Ac—Leu—Asn—Phe—Pro—Ile—Ser—OH | — |
| (HIV2) | Ac—Leu—Asn—Leu—Pro—Val—Ala—NH$_2$ | — |

*This peptide used as control to determine relative rate of the other peptides.

A series of HIV-1 protease inhibitors based on MVT-101 (Ac-Thr-Ile-Nle-Ψ[CH$_2$NH]Nle-Gln-Arg-NH$_2$) that possess a keto-methylene-isostere dipeptide unit were prepared by conventional solid phase synthesis using the p-methylenebenzydrylamine resin. This procedure utilized the general synthetic scheme by Kaltenbronn et al., *J. Med. Chem.* 33, 838-845 (1990) to prepare the ketomethylene isostere dipeptides, as described above.

These peptide analogs were assayed in solution for their ability to inhibit retroviral protease (HIV-1) by a fluorometric assay for HIV protease as described by Toth and Marshall, *Int. J. Peptide Protein Res.* 36, 546-550 (1990), and in U.S. Pat. No. 5,011,910.

Table 2, below, sets forth the median inhibitory concentration, IC$_{50}$, (μM) for the compounds thus tested. In those cases where the isomers were resolved, the activities of both isomers are shown.

TABLE 2.

Keto-Methylene isosteric replaced amide bond inhibitors of HIV protease.

| Peptide | IC$_{50}$ (μM) |
|---|---|
| Abz—Thr—Ile—NleΨ(K)Nle—Gln—Arg—NH$_2$ | 0.0063 |
| | 0.423 |
| Abz—Thr—Ile—Nle—Ψ(K)2-Nal—Gln—Arg—NH$_2$ | 0.0048 |
| Abz—Thr—Ile—PheΨ(K)Ala—Gln—Arg—NH$_2$ | 0.033 |
| Qua—Thr—Ile—NleΨ(K)2-Nal—Gln—Arg—NH$_2$ | 1.54 |
| | 0.0046 |
| Qua—Ile—NleΨ(K)2-Nal—Gln—Arg—NH$_2$ | 0.0085 |
| Qua—NleΨ(K)2-Nal—Gln—Arg—NH$_2$ | 96% at 10 μM |
| Qui—Thr—Ile—NleΨ(K)Nle—Gln—Arg—NH$_2$ | 0.029 |
| | 1.47 |
| Qui—Ile—NleΨ(K)Nle—Gln—Arg—NH$_2$ | 0.087 |
| | 1.37 |
| Qui—Nle—Ψ(K)Nle—Gln—Arg—NH$_2$ | 2% at 10 μM |
| | 26% at 10 μM |
| Qui—Thr—Ile—NleΨ(K)2-Nal—Gln—Arg—NH$_2$ | 1.24 |
| | 0.0073 |
| Qui—Ile—NleΨ(K)2-Nal—Gln—Arg—NH$_2$ | 1.60 |
| | 0.0102 |
| Qui—NleΨ(K)2-Nal—Gln—Arg—NH$_2$ | N.D. |
| Qui—Thr—Ile—NleΨ(K)2-Nal—Gln—NH$_2$ | 1.11 |
| | 8.08 |
| Qui—Ile—NleΨ(K)2-Nal—Gln—NH$_2$ | 54% at 10 μM |
| Qui—NleΨ(K)2-Nal—Gln—NH$_2$ | 7% at 10 μM |

K = COCH$_2$

Amino acids are shown herein either by standard one letter or three letter abbreviations as follows:

| Abbreviated | Designation | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Other standard abbreviations used in the peptide sequences herein are:
Nle = norleucine,
Nva = norvaline,
MeNle = N-methyl-norleucine,
Cha = cyclohexylalanine,
PnF = p-nitrophenylalanine,
Cle = 1-aminocyclopentanecarboxylic acid, and
Ac = acetyl.
Abz = o-aminobenzoic acid
Qua = quinaldic acid
Qui = quinoxalic acid
2-Nal = β-naphthylalanine Various other examples will be apparent to the person skilled in the art after reading the present disclosure without departing from the spirit and scope of the invention. For example, various derivatives of the disclosed peptides having substantially similar antiviral activity can be readily made by appropriate substitutions during the peptide synthesis or by subsequent modification. It is intended that all such other examples be included within the scope of the appended claims.

What is claimed is:

1. An inhibitor of HIV protease selected from the group consisting of
Abz-Thr-Ile-NleΨ(K)Nle-Gln-Arg-NH$_2$,
Abz-Thr-Ile-Nle-Ψ(K)2-Nal-Gln-Arg-NH$_2$,
Abz-Thr-Ile-PheΨ(K)Ala-Gln-Arg-NH$_2$,
Qua-Thr-Ile-NleΨ(K)2-Nal-Gln-Arg-NH$_2$,
Qua-Ile-NleΨ(K)2-Nal-Gln-Arg-NH$_2$,
Qua-NleΨ(K)2-Nal-Gln-Arg-NH$_2$,
Qui-Thr-Ile-NleΨ(K)Nle-Gln-Arg-NH$_2$,
Qui-Ile-NleΨ(K)Nle-Gln-Arg-NH$_2$,
Qui-NleΨ(K)Nle-Gln-Arg-NH$_2$,
Qui-Thr-Ile-NleΨ(K)2-Nal-Gln-Arg-NH$_2$,
Qui-Ile-NleΨ(K)2-Nal-Gln-Arg-NH$_2$,
Qui-NleΨ(K)2-Nal-Gln-Arg-NH$_2$,
Qui-Thr-Ile-NleΨ(K)2-Nal-Gln-NH$_2$,
Qui-Ile-NleΨ(K)2-Nal-Gln-NH$_2$, and
Qui-NleΨ(K)2-Nal-Gln-NH$_2$
and wherein K is COCH$_2$.

* * * * *

UNITED STATES PATENT AND TRADEMARK OFFICE
CERTIFICATE OF CORRECTION

PATENT NO. : 5,086,165

DATED : February 4, 1992

INVENTOR(S) : GARLAND R. MARSHALL AND MIHALY V. TOTH

It is certified that error appears in the above-identified patent and that said Letters Patent are hereby corrected as shown below:

col. 8, line 54, "$K_m32$" should read -- $K_m$ --.

col. 8, line 54, "$V_{max}32$" should read -- $V_{max}$ --.

Signed and Sealed this

Eighteenth Day of January, 1994

Attest:

BRUCE LEHMAN

Attesting Officer    Commissioner of Patents and Trademarks